United States Patent
Loontjens et al.

(10) Patent No.: US 6,448,394 B1
(45) Date of Patent: Sep. 10, 2002

(54) PROCESS FOR THE PREPARATION OF AN N-ALKYL OR N-ARYL CARBAMOYL DERIVATIVE

(75) Inventors: Jacobus A. Loontjens, Meerssen; Bartholomeus J. M. Plum, Ulestraten, both of (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/815,268

(22) Filed: Mar. 23, 2001

Related U.S. Application Data

(63) Continuation of application No. PCT/NL99/00589, filed on Sep. 21, 1999
(60) Provisional application No. 60/114,383, filed on Dec. 29, 1998.

(30) Foreign Application Priority Data

Sep. 24, 1998 (NL) .............................................. 1010175

(51) Int. Cl.[7] .......................................... C07D 223/10
(52) U.S. Cl. ..................................................... 540/525
(58) Field of Search ......................................... 540/525

(56) References Cited

U.S. PATENT DOCUMENTS

| | | | |
|---|---|---|---|
| 3,957,756 A | 5/1976 | Ribka et al. .............. 260/239.3 |
| 4,223,112 A | * 9/1980 | Hedrick et al. ............. 525/432 |
| 4,302,351 A | 11/1981 | Gras et al. .................. 252/182 |
| 5,200,498 A | * 4/1993 | Udipi et al. ................. 528/323 |
| 5,972,237 A | * 10/1999 | Muller et al. ........... 252/186.39 |
| 6,228,980 B1 | * 5/2001 | Loontjens et al. .......... 528/480 |

FOREIGN PATENT DOCUMENTS

| | | |
|---|---|---|
| DE | 27 12 931 A | 9/1978 |
| DE | 28 30 206 A | 1/1980 |
| GB | 1 415 730 A | 11/1975 |

* cited by examiner

*Primary Examiner*—Bruck Kifle
(74) *Attorney, Agent, or Firm*—Pillsbury Winthrop LLP

(57) ABSTRACT

The invention relates to a process for the preparation of an N-alkyl or N-aryl carbamoyl derivative in which an amine is contacted with a carbonic acid derivative according to the general formula:

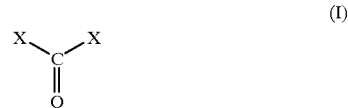

where fragments X in the form of XH are a lactam, oxime, imide or triazole. In particular the invention relates to the preparation of a blocked isocyanate according to a process in which no isocyanate is used. The invention also relates to the use of the N-alkyl or N-aryl carbamoyl derivative prepared according to the process according to the invention in a coating.

7 Claims, No Drawings

PROCESS FOR THE PREPARATION OF AN N-ALKYL OR N-ARYL CARBAMOYL DERIVATIVE

This is a continuation of International Application No. PCT/NL99/00589 filed Sep. 21, 1999 which designated the U.S., and that international application was published under PCT Article 21 (2) in English, and claims benefit of Provisional application Ser. No. 60/114,383, filed Dec. 29, 1998.

The invention relates to a process for the preparation of an N-alkyl or N-aryl carbamoyl derivative, and in particular a blocked isocyanate. A blocked isocyanate is a compound which contains an isocyanate with a blocking agent.

Blocked isocyanates are used in the preparation of polyurethanes and polyurea. A blocked isocyanate can in a stable manner be mixed with a polyol at temperatures of up to, for example, 150° C. Upon an increase in temperature, the blocking agent splits off from the isocyanate group, so that the released isocyanate can react with the polyol that is present to form a polyurethane.

A method for the production of blocked isocyanates is described in GB-A-1415730. GB-A-1415730 describes a process wherein an N-(1-chloro-1-alkenyl)-carbonic acid chloride is reacted with an amine, to form a blocked isocyanate.

A process for the preparation of an N-alkyl or N-aryl carbamoyl derivative is disclosed in DE-A-2712931. In said process, an isocyanate is contacted with caprolactam, as a result of which a caprolactam-blocked isocyanate is formed.

A drawback of the process disclosed in DE-A-2712931 is that a reaction with isocyanate involves safety risks.

The aim of the invention is to provide a safer process.

This aim is achieved in that an amine is contacted with a carbonic acid derivative according to the following general formula:

(I)

where fragments X in the form of XH are a lactam, oxime, imide or triazole.

In the process according to the invention no isocyanate is present in the reaction mixture.

An advantage of the process according to the invention is that a blocked isocyanate is formed in which no free isocyanate is present anymore.

Since the known reaction disclosed in DE-A-2712931 does not proceed quantitatively, a small amount of free isocyanate remains present in the reaction mixture. To reduce the vapor pressure of this free isocyanate, the isocyanate is often trimerized by means of a temperature increase before being contacted with lactam. This is done in particular for isophorone diisocyanate (IPDI) and hexamethylene diisocyanate (HMDI). An advantage and a consequence of the fact that no free isocyanate is present in the reaction mixture in the process according to the invention, is that there is no need to carry out the above-mentioned trimerization reaction.

A further advantage of the process according to the invention is that it can be used to prepare an N-alkyl or N-aryl carbamoyl derivative of which the nitrogen is secondary and the derivative is a lactam, oxime, imide or triazole. These are compounds that cannot be prepared via the known isocyanate route.

In the framework of this invention amines may be mono-, di-, tri-, polyamines or mixtures of these, Examples of di- and triamines are diamino octane, diamino nonane, diamino dodecane, trisamino nonane, diamino dioxydecane, diamino dioxododecane, bishexamethylene trisamine and Jeffamines. Other suitable amines are oligomers, as reaction products of two components. Examples of oligomers are the reaction products of hexamethylene diamine with adipic acid, urea, carbonyl biscaprolactamate (CBC) and with 1 or 2 caprolactam molecules An advantage of the process according to the invention for the preparation of blocked isocyanates on the basis of oligomeric amines is the fact that the fragments (X), which are split off in the reaction between the carbonic acid derivative and the amine, can readily be removed from the reaction mixture as XH. This contrasts with the removal of the triethylamine salt that is released in the preparation of blocked isocyanates on the basis of phosgene and triethylamine.

Contacting an amine with the carbonic acid derivative can optionally be effected in a solvent. Preferably, this is done by dissolving the carbonic acid derivative according to formula I in a suitable first solvent. Suitable solvents are generally non-protic solvents such as esters, ethers, cyclic carbonates, cyclic amides and hydrocarbons. Subsequently the amine, dissolved in a second solvent, can slowly be added, with continuous stirring, to the solution of the carbonic acid derivative. Second solvents are preferably also chosen from the same group of non-protic solvents.

Preferably, the first and the second solvent are the same.

After the addition of the dissolved amine the mixture is stirred for some time at a temperature between room temperature and 150° C. Above 150° C. the blocking agent can readily be split off. Stirring preferably takes place at a temperature between 50 and 100° C., after which the N-alkyl or N-aryl carbamoyl derivative formed can be separated from the reaction mixture according to known techniques.

The product obtained by the process according to the invention can be very widely applied in technically different fields, both in thermosetting and in thermoplastic applications. Examples are powder paint compositions, coating systems based on water or solvent and can or coil coating systems, inks, toners, film formers for glassfibre sizings, adhesives, hot melts and in rubber compositions.

Unmodified or partly modified polymers according to the invention can generally be used in powder paint compositions, in can or coil coating compositions and in solvent-based coating compositions.

According to a preferred embodiment of the invention the products obtained by the process according to the invention can be used as a crosslinker in thermosetting powder paint compositions.

Thermosetting powder paints have a better resistance to chemicals than thermoplastic powder paints. As a result of this, intensive efforts have for a long time been made to develop crosslinkers and polymers for thermosetting powder coatings. Attempts are still being made to find binder compositions for thermosetting powder paints with a good flow behaviour, good storage stability and a good reactivity. A thermosetting powder paint binder composition generally contains more than 50 wt. % polymer and less than 50 wt. % crosslinker.

The product obtained according to the invention can be used in a powder paint composition as a crosslinker in combination with a hydroxyl functional polymer.

The hydroxyl functional polymer is preferably a polyester, a polyacrylate or a mixture of both. Preferably, the polyester has a hydroxyl number of between 20 and 100 mg of KOH/gram of resin and an acid number of less than 10 mg of KOH/gram of resin. Preferably, the polyacrylate has a hydroxyl number of between 40 and 150 mg of KOH/gram of resin and an acid number of less than 20 mg of KOH/gram of resin.

The weight ratio between the polymer containing hydroxyl groups and the crosslinker can be between about 95:5 and about 50:50, and preferably between 93:7 and 70:30. This ratio depends on, among other factors, the hydroxyl number of the polymer.

The hydroxyl functional polymers can be mixed with the blocked crosslinker by extrusion, for example, at a temperature of about 100° C. The curing takes place at temperatures of, for example, between about 130° C. and about 170° C. (in, for example, about 10–40 minutes), and preferably above about 150° C.

Additives, such as for example fillers, catalysts, curing agents, flow agents and/or stabilizers and, if required, pigments, can be added to the coating systems, preferably before the extrusion.

Suitable polyesters can be obtained via customary preparation methods from carboxylic acids or equivalents thereof. The use of mainly aromatic carboxylic acids is preferred. Examples include phthalic acid, isophthalic acid, terephthalic acid, pyromellitic acid, trimellitic acid, 3,6-dichlorophthalic acid, tetrachlorophthalic acid and, in so far as available, equivalents like anhydrides, acid chlorides or lower alkyl esters thereof. Generally, the carboxylic acid component comprises at least 50 wt. %, and preferably at least 70 mol %, isophthalic acid and/or terephthalic acid.

Preferably, the diol component of the polyester is an aliphatic diol. Examples include ethylene glycol, propane-1,2-diol, propane-1,3-diol, butane-1,2-diol, butane-1,4-diol, butane-1,3-diol, 2,2-di-methylpropane diol-1,3 (=neopentyl glycol), hexane-1,6-diol, 2,2-[bis(2-hydroxyethoxy)] phenylpropane and smaller quantities of polyols, such as for example glycerol, hexane triol, pentaerythritol, sorbitol, trimethylol ethane, trimethylol propane and tris-(2-hydroxy)-isocyanurate, can be used as alcohols. It is also possible to use epoxy compounds instead of diols and polyols, respectively. The alcohol component preferably contains at least 50 mol % neopentyl glycol.

In addition, the polycarboxylic acids applied can be cycloaliphatic and/or acyclic polycarboxylic acids. Examples include cyclohexane dicarboxylic acid, tetrahydrophthalic acid, hexahydroendomethylene tetrahydrophthalic acid, azelainic acid, sebacic acid, decane dicarboxylic acid, adipic acid, succinic acid and maleic acid. The amount of cycloaliphatic and/or acyclic polycarboxylic acid can be up to about 30 mol %, and preferably up to about 20 mol %, relative to the total of carboxylic acids. Hydroxycarboxylic acids and/or, optionally, lactones can also be used. Examples include 12-hydroxylstearic acid, epsilon caprolactone and hydroxypivalic ester of neopentyl glycol. Monocarboxylic acids can also be added in minor amounts, for example less than 5% by weight, during the preparation. Examples include benzoic acid, tert.-butylbenzoic acid, hexahydrobenzoic acid and saturated aliphatic monocarboxylic acids.

The polyesters can be prepared by esterification or transesterification known to those skilled in the art. Optionally, customary catalysts can be used. Examples include dibutyl tin oxide or tetrabutyl titanate. The preparation conditions and the COOH/OH ratio are chosen so that a polyester resin having the desired hydroxyl number and acid number is obtained, for example a hydroxyl number of between about 20 and about 100 mg of KOH/gram of resin and an acid number of less than about 10 mg of KOH/gram of resin.

Preferably, polyesters are based on about 40–100 mol % isophthalic acid and about 0–60 mol % terephthalic acid as dicarboxylic acids (wherein the quantities of isophthalic acid and terephthalic acid together amount to 100 mol %). Preferably, the amount of isophthalic acid is more than 60 mol %.

Optionally, the polyester can also be based on more than two dicarboxylic acids.

The hydroxyl functional acrylate resin can be, for example, based on hydroxyl (meth)acrylate, hydroxypropyl (meth)acrylate and methyl (meth)acrylate. The resin can also be based on (meth)acrylic acid and alkyl esters of (meth)acrylic. Examples include ethyl (meth)acrylate, isopropyl (meth)acrylate, n-butyl (meth)acrylate, n-propyl (meth)acrylate, isobutyl (meth)acrylate, ethylhexyl acrylate and/or cyclohexyl (meth)acrylate. Vinyl compounds such as, for example, styrene can also be used The glass transition temperature (Tg) of the product obtained by process according to the invention lies between 10 and 150° C., preferably between 50° C. and 110° C., depending on the selected starting materials and the molecular weight.

It has been found that use of the product according to the invention in binder compositions in combination with hydroxy functional polymers results in a combination of highly desirable properties such as for example good flow behaviour and good resistance to chemicals, desired gloss without bubble formation at the surface up to and including layer thicknesses of at least 120 μm, a high resistance to boiling water and salt spray, a high resistance to scratching, good mechanical properties and good colour stability of the powder coating.

The preparation of thermosetting powder coatings in general and the chemical reactions for curing powder paints to form cured coatings are described by Misev in Powder Coatings, Chemistry and Technology (1991, John Wiley) on pp. 42–54, p. 148 and pp. 224–226. A thermosetting binder composition is generally defined as the resinous part of the powder paint consisting of polymer and crosslinker.

If so desired, the usual additives can be used in the binder composition and in the powder paint system according to the invention, such as for example pigments, fillers, degassing agents, flow agents and stabilizers. Suitable pigments are for example inorganic pigments, such as for example titanium dioxide, zinc sulphide, iron oxide and chromium oxide, and also organic pigments such as for example azo compounds. Suitable fillers are for example metal oxides, silicates, carbonates and sulphates.

Primary and/or secondary antioxidants, UV stabilizers such as quinones, (sterically hindered) phenolic compounds, phosphonites, phosphites, thioethers and HALS compounds (hindered amine light stabilizers) can for example be used as stabilizers.

Examples of degassing agents are benzoin and cyclohexane dimethanol bisbenzoate. The flow agents include for example polyalkylacrylates, fluorohydrocarbons and silicone fluids. Other suitable additives are for example additives for improving tribocharging, such as sterically hindered tertiary amines that are described in EP-B-371528.

Powder paints according to the invention can be applied in the usual manner, for example by electrostatically spraying the powder onto an earthed substrate and curing the coating by exposing it to heat at a suitable temperature for a sufficient length of time. The applied powder can for example be heated in a gas oven, an electric oven or with the aid of infrared radiation.

Thermosetting powder paint compositions intended for industrial applications are described in a general sense in Powder Coatings, Chemistry and Technology, Misev, pages 141–173 (1991).

Compositions according to the present invention can be used in powder paints for use on, for example, metal, wooden and plastic substrates. The coatings are also suitable for use in the automotive industry for coating parts and accessories.

As is evident from, for example, 'Resins and curing agents for thermosetting powder coatings' (by Kapilow and Sammel, Vol. 59, July 1987, pp. 39–47, Journal of Coatings Technology), coatings based on a solvent or water are not related to thermosetting powder paints, for powder paints must meet requirements relating to, for example, the melting point of the binder, the rheological properties, the reactivity and the stability, that do not apply to 'wet' coatings. If the molecular weight, the viscosity and the glass transition temperature of the hydroxyl functional polymers are adapted through the choice of monomers, these polymers, in combination with the crosslinker according to the invention, can—surprisingly—also be used as starting compound for solvent- or water-based coatings.

According to a further preferred embodiment of the invention the product obtained by the process according to the invention is applied as a crosslinker in a binder system for a coil coating or for a can coating.

Suitable binder systems in these applications are hydroxyl functional polymers such as polyesters or polyacrylates. Suitable solvents in these applications are esters or hydrocarbons. The catalysts which can be used in coil or can coatings are well known from polyurethane chemistry. Examples of catalysts are Sn catalysts.

Coil coatings can be obtained via commonly known processes as described for example in "Coil Coatings" by Joseph E. Gaske (Federation of Societies for Coatings Technology, February 1987, pp. 7–19).

The curing conditions and additives can be chosen to depend on the desired peak metal temperature (PMT) and the nature and thickness of the substrate. The curing time will generally be between about 20 and about 70 seconds at temperatures of between about 250° C. and about 400° C. and a PMT of between 204° C. and 249° C.

Suitable substrates include for example steel, tin-plated steel and aluminium.

The coil coatings according to the invention are suitable for use as primer and as top coat and can for example be used as coating for household equipment such as fridges, freezers, microwave ovens, ovens and boilers, as coating for caravans and as coating for facade cladding.

The resin composition according to the invention also yields good results in the can coating industry, in which the desired layer thickness is generally thinner and in which the curing conditions differ from the conditions in the preparation of coil coatings.

Can coatings can be obtained via processes of the kind described in for example 'Organic Coatings—Science and Technology, Volume 2: Applications, Properties and Performance' by Z. W. Wicks et al. (Wiley-Interscience, 1994, pp. 284–290).

The curing conditions and additives can be selected to depend on the desired application and the nature and thickness of the substrate. The curing time will generally lie between a few seconds and tens of minutes at temperatures of between about 100° C. and about 220° C.

Suitable substrates include for example steel, tin-plated steel (ETP, Electrolytic Tin Plate), chromium-plated steel (ECCS, Electrolytic Chromium—Chromium oxide Steel) and aluminium.

The coatings according to the invention are suitable for use as interior and exterior coatings and can be used for example as coatings for beer cans, cans for other beverages ('2 and 3 piece'), spray cans, can ends, tubes, drums, cigar boxes and fish cans (the so-called 'drawn-redrawn (DRD)', 'draw-wall ironed (DWI)' cans). They can be used in pigmented or in unpigmented compositions.

The use of the exterior coating is important primarily from a decorative viewpoint, for giving the substrate a saleable appearance. It protects the metal from corrosion and the coating also serves as a label.

The interior coating is mainly intended on the one hand to protect the contents of the can against the influences of the metal and on the other to protect the metal against the contents of the can.

The type of monomers to be used to prepare the polyester, the crosslinkers and the curing conditions can be chosen to depend on the desired use.

The systems according to the invention can be used in pigmented an in unpigmented compositions.

If so desired, the usual additives such as pigments, fillers, stabilizers, dispersing agents, flow-promoting agents and defoaming agents can be added to the binder system according to the invention.

The invention will be elucidated below on the basis of the following examples.

EXAMPLE I

The preparation of the caprolactam-blocked tetramethylene diisocyanate

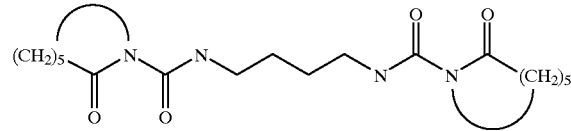

54.4 g (0.2 mol) carbonyl-bis-caprolactam was dissolved in 200 ml ethyl acetate at 78° C. In 20 minutes 88 g (0.1 mol) 1,4-diamine butane, dissolved in 20 ml ethyl acetate, was added dropwise. A white suspension formed. After four hours the reaction was stopped. The white product was isolated by filtration. The caprolactam that was present was removed by means of sublimation in the vacuum oven at 60° C. Caprolactam-blocked tetramethylene diisocyanate, a white solid, was obtained in a yield of 80%.

EXAMPLE II

Preparation of the caprolactam-blocked tris(isocyanatoethyl)amine

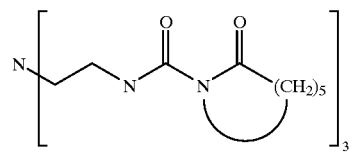

75.6 g (0.3 mol) carbonyl-bis-caprolactam was dissolved in 200 ml ethyl acetate at 78° C. In 20 minutes 14.6 g (0.1 mol) tris-(2-amine-ethyl) amine, dissolved in 20 ml ethyl acetate, was added dropwise. The clear suspension was stirred overnight at 78° C. The solution was washed three times with 250 ml water (with some NaCl) to remove the caprolactam. The solution was dried with NaSO$_4$. The NaSO$_4$ was removed by filtration and the ethyl acetate was removed by means of the rotavapor. Caprolactam-blocked tris (isocyanato-ethyl)amine proved to be a coloured oil and was obtained in a yield of 99%.

EXAMPLE III

Preparation of N,N-dibutyl-N-(caprolactamate carboxylamine)

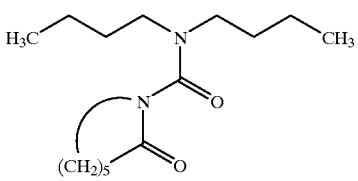

2.5 g (10 mmol) carbonyl-bis-caprolactam (CBC) was added to 10 ml dibutyl amine (60 mmol) at 160° C. This coloured solution was stirred overnight at 160° C. Everything was cooled. 150 ml ethyl acetate was added to the solution. The solution was then extracted with three times 150 ml water (buffer pH=5). The ethyl acetate was removed by means of the rotavapor. It is found that dibutyl amine was still present in the product. This was removed by distillation. N,N-dibutyl-N-(caprolactamate carboxyl) amine was an oil. The purity was 80%. The yield relative to CBC was 99%.

EXAMPLE IV

Preparation of the caprolactam-blocked hexamethylene diisocyanate

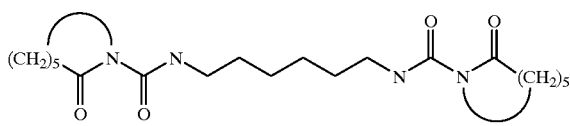

151.2 g (0.6 mol) carbonyl-bis-caprolactam was dissolved in 400 ml ethyl acetate at 78° C. In 15 minutes 34.8 g (0.3 mol) 1,6-diamine hexane, dissolved in 40 ml ethyl acetate, was added dropwise. The clear suspension was stirred overnight at 78° C. The solution was washed four times with 250 ml water (with some NaCl) to remove the caprolactam. The solution was dried with NaSO$_4$. The NaSO$_4$ was removed by filtration and the ethyl acetate was removed by means of the rotavapor. After recrystallization in ethyl acetate caprolactam-blocked hexamethylene diisocyanate was obtained as a white solid in a yield of 85%.

EXAMPLE V

Preparation of the caprolactam-blocked octamethylene diisocyanate

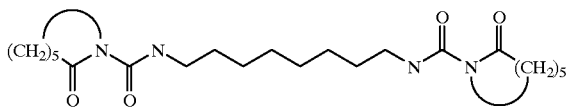

252 g (1.0 mol) carbonyl-bis-caprolactam was dissolved in 400 ml ethyl acetate at 78° C. In 15 minutes 75.1 g (0.5 mol) 1,8-diamine octane, dissolved in 150 ml ethyl acetate, was added dropwise. The clear solution was stirred for two hours at 78° C. The solution was washed three times with 500 ml water (with some NaCl) to remove the caprolactam. The clear solution was cooled to 5° C. The product crystallized out and was isolated by filtration (yield=47%). The solution was concentrated to 100 ml and cooled to 5° C. Again, the product crystallized out (yield=38%), The product was isolated by filtration. Subsequently, the solution was concentrated to 50 ml. The product again crystallized out and was isolated by filtration (yield=6%).

The various batches were dried at 40° C. and in a vacuum. Caprolactam-blocked octamethylene diisocyanate proved to be a white solid. The overall yield was 91%.

EXAMPLE VI

Preparation of the caprolactam-blocked 1,8-diisocyanato, 4-(isocyanatomethyl)nonane

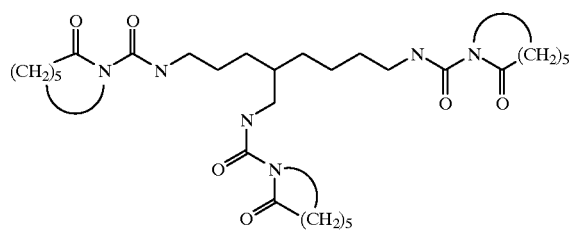

302.4 g (1.2 mol) carbonyl-bis-caprolactam was dissolved in 400 ml ethyl acetate at 78° C. In one hour 69.3 g (0.4 mol) triamino nonane, dissolved in 100 ml ethyl acetate, was added dropwise. The reaction was monitored by means of TLC. After 3 hours the clear solution was cooled to room temperature and extracted 4 times with 500 ml water (with some NaCl). The solution was then dried with NaSO$_4$. The NaSO$_4$ was removed by filtration and the ethyl acetate was removed by means of the rotavapor. The product was dried at 75° C. and in a vacuum. Caprolactam-blocked of 1,8-diisocyanato, 4-(isocyanatomethyl) nonane was obtained pure, as a lightly coloured oil (yield=99%).

What is claimed is:

1. Process for the preparation of a blocked isocyanate of an N-alkyl or N-aryl compound, comprising contacting a primary, secondary mono-, di-, tri- or poly- amine or mixture thereof, at a temperature between room temperature and 160° C. with carbonylbiscaprolactam, whereby, during the reaction, caprolactam is split off.

2. Process according to claim 1, wherein the amine or mixture thereof is diamino butane.

3. Process according to claim 1, wherein the amine or mixture thereof is tris-(2-amino-ethyl) amine.

4. Process according to claim 1, wherein the amine or mixture thereof is a diamine hexane.

5. Process according to claim 1, wherein the amine or mixture thereof is a diamino octane.

6. Process according to claim 1, wherein the amine or mixture thereof is a triamino nonane.

7. Process according to claim 1, wherein the amine or mixture thereof comprises diamino octane, diamino nonane, diamino dodecane, trisamino nonane, diamino dioxydecane, diamino dioxododecane or bishexamethylene trisamine.

* * * * *